United States Patent [19]

Liddell et al.

[11] Patent Number: 5,691,174
[45] Date of Patent: Nov. 25, 1997

[54] PRODUCTION OF PLASTICS MATERIALS FROM MICROORGANISMS

[75] Inventors: John Macdonald Liddell, Stockton on Tees; Timothy John Locke, Middlesbrough, both of United Kingdom

[73] Assignee: Zeneca Limited, London, England

[21] Appl. No.: 530,332

[22] PCT Filed: Apr. 7, 1994

[86] PCT No.: PCT/GB94/00741

§ 371 Date: Oct. 10, 1995

§ 102(e) Date: Oct. 10, 1995

[87] PCT Pub. No.: WO94/24302

PCT Pub. Date: Oct. 27, 1994

[30] Foreign Application Priority Data

Apr. 14, 1993 [GB] United Kingdom ............... 9307674

[51] Int. Cl.⁶ .................. C12P 7/62; C12P 7/48; C12N 1/08
[52] U.S. Cl. .................. 435/135; 435/144; 435/267; 435/270; 435/317.1; 435/800; 435/803; 435/820; 435/829
[58] Field of Search ................ 435/135, 144, 435/829, 820, 800, 803, 317.1, 267, 270

[56] References Cited

FOREIGN PATENT DOCUMENTS 145 233  6/1985  European Pat. Off. .

OTHER PUBLICATIONS

Biotech Abs 94–08787 WO9410289 (May 11, 1994).
Ito et al: "Degradation of RNA in *Escherichia coli* induced by sodium chloride", Agricultural and Biological Chemistry, vol. 41, No. 2, 1977, pp. 257–263 (see whole document).
Hughes: "Action of oxygenated water on DNA in the presence of ferrous ions and light", Chemical Abstracts, vol. 70, No. 7, 1969, abstract No. 25618r, p. 8, see abstract & Biochemical and Biophysical Research Communications, vol. 166, No. 3, 1968, pp. 720–722.

*Primary Examiner*—Herbert J. Lilling
*Attorney, Agent, or Firm*—Cushman Darby & Cushman IP Group of Pillsbury Madison & Sutro LLP

[57] ABSTRACT

A plastic is recovered from microorganisms containing it by chemically solubilising non plastic material with an oxidising agent in the presence of a chelating agent.

12 Claims, No Drawings

PRODUCTION OF PLASTICS MATERIALS FROM MICROORGANISMS

This application claims benefit of international application PCT/GB94/00741 filed Apr. 7, 1994.

This invention relates to the recovery of plastics materials from microorganisms.

It is known to produce plastics materials which can be formed into shaped articles for example by heating them (plastic) from microorganisms. These are generally polyhydroxyalkanoates, for example polymers which comprise hydroxybutyric acid residues (PHB). The homopolymer is found widely in naturally occurring microorganisms and it is known from European patent specifications 52499 and 69497 that copolymers may also be produced. Co-polymers of hydroxybutyric and hydroxyvaleric acid have now become well known.

Although it is possible to grow micro organisms which contain large quantities of plastic for example 60% or more and even 80% or more by weight based on the dry cell weight of the microorganisms, it is normally necessary to remove other components of the cellular material from it before the plastic can be used satisfactorily.

It is known from European patent specification 145,233 that digestion of the cells with certain enzymes (proteases and phospholipases) is useful in this respect and treatment with surfactants is also disclosed. After such treatment and washing it was disclosed that the product could be further treated with hydrogen peroxide. Whilst the multistage process produces product of good purity, it is complex and consequently expensive.

We have now found that the process may be improved by using an oxidising agent (for example hydrogen peroxide) in the presence of a chelating agent. It is then possible to carry out an oxidation treatment in the presence of non-plastic cellular material or decomposition products thereof which enables a separation stage for the removal of such unwanted material prior to the oxidation treatment to be omitted.

It is thus possible to carry out a decomposition and/or solubilisation stage of such material (for example with one or more enzymes as aforesaid) and to treat the product of such a stage with an oxidising agent with less or even no intermediate purification.

We have also surprisingly found that good results may be obtained if the oxidation stage is the first chemical treatment and indeed even if it is the only chemical treatment. It may however be desirable in order to secure particularly high level of purity to carry out a subsequent chemical treatment also.

This invention comprises a process of recovering plastic, from a plastic producing microorganism in which non plastic material is removed from the plastic by a process which comprises chemically reacting non plastic material of the microorganisms in a stage of chemical solubilisation of non plastic material with an oxidising agent in the presence of a chelating agent.

The invention also comprises a process of producing a plastic, for example PHB which comprises growing a plastic producing microorganism under conditions conducive to plastic accumulation characterised in that non plastic material is removed from the product by a process which comprises chemically reacting non plastic material of the microorganism, optionally after physical treatment to condition the microorganism for subsequent processing, for example by disrupting its cell wall by a stage of chemical solubilisation of non plastic material with an oxidising agent in the presence of a chelating agent which stage is preferably the first or only chemical treatment stage.

The quantity of the chelating agent used varies according to a number of factors. In order to grow the microorganisms it is necessary to supply inorganic nutrients, for example iron, manganese and/or copper ions, and in general the quantity of chelating agent must be increased if the quantity of polyvalent metal ions is increased. If the quantity of chelating agent is too high or too low the process becomes less efficient, and the optimum quantity required should be established experimentally.

Suitable chelating agents include ethylenediamine tetra acetic acid, citric acid and diethylene triamine pentamethylene phosphonic acid and nitrilo triacetic acid or polyphosphates for example sodium tripolyphosphate.

The quantity of oxidising agent present is suitably proportionate to the quantity of non plastic cellular material to be removed. In general 5 to 50 for example 10 to 30 oxygen equivalents of oxidising agent per kilogram of non plastic cellular material may be used. By oxygen equivalent is meant the quantity of oxidising agent equivalent to a gram atom of active oxygen.

The oxidising agent may be for example a chlorine containing oxidising agent for example chlorine, a chlorate, perchlorate or hypochlorite or chlorine dioxide. It is preferred however to use hydrogen peroxide either as such or as a compound which produces hydrogen peroxide in situ or acts as an equivalent thereof, suitably a percarboxylic acid, for example peracetic acid, a perborate or a percarbonate. It is preferred however to use hydrogen peroxide supplied as such.

The temperature of the chemical solubilisation may be for example 40° to 200° C. suitably 70°–180° C. for example 70° to 160° C.

It may be desirable to introduce the oxidising agent continuously or intermittently during the process rather than introducing the whole amount at the beginning especially at high temperatures, for example 120° to 200° C. because the losses of oxidising agent due to thermal decomposition may be minimised thereby.

If desired the process may include a stage of high temperature treatment of the organisms for example at a temperature of 100° to 200° C. preferably 120° to 180° C. for a time sufficient to cause substantial degradation of nucleic acids of the microorganisms before the initial stage of chemical decomposition.

It is preferred to combine the disruption of the cell walls, decomposition of nucleic acids and solubilisation of non plastic cellular material in a single step by carrying out the process of the invention at a temperature of 100° to 200° C. and preferably 120° to 180° C. The process may be carried out more rapidly at such temperatures.

The process may comprise only one stage of chemical decomposition or if desired subsequent treatments with for example oxidising agents, surfactants and/or oxygen may be carried out, preferably after separating the plastic from the other products of the chemical decomposition stage for example by centrifuging or preferably filtering. A physical treatment before, during or after the first chemical decomposition stage may be carried out to increase the plastic particle sizes.

It is preferred to operate the process under substantially neutral conditions, for example at pH4 to 10 and preferably pH5 to 9 and more preferably pH6 to 8.

A solids concentration of microorganisms 50 to 300 g and preferably 60 to 250 g per liter may be employed.

EXAMPLE 1

A strain of *Alcaligenes eutrophus* was grown in batch culture in an aqueous medium on a mixture of glucose and propionic acid under phosphorus limitation to give a culture containing 155 g/l of cells containing 71.5% of a 3-hydroxybutyrate (HB)/3-hydroxyvalerate (HV) copolymer with a hydroxyvalerate content of 10% (the remainder of the polymer being hydroxybutyrate).

A sample of the cells was first heat treated at 150° C. for 80 seconds at pH6.5. These heat shocked cells were then treated with a proteolytic enzyme (EC 3.4.21.14) at pH8, 70° C. for 2 hours. A detergent (Synperonic A11) was added to the proteolysed cell suspension resulting from the proteolytic treatment and the treatment continued for a further 2 hours with maintenance of the same temperature and pH conditions. At the end of this time the pH of the suspension was adjusted to pH7, the temperature raised to 80° C. and sodium citrate added to give a final concentration of 35 mM. 35% w/v hydrogen peroxide solution was added to give a final aqueous phase concentration of 5.0% w/v of hydrogen peroxide. The temperature and pH conditions were maintained for 10 hours. The resulting polymer solids were recovered by centrifugation, washing and drying.

Analysis of the polymer product for impurities indicated that the concentration of residual nitrogen was 880 ppm corresponding to a protein concentration of approximately 5500 ppm.

The polymer product was thus considered to be 99.5% pure poly-3-hydroxybutyrate/3-hydroxyvalerate.

EXAMPLE 2

A strain of *Alcaligenes eutrophus* was grown in batch culture in an aqueous medium on a mixture of glucose and propionic acid under phosphorus limitation to give a culture containing 164 g/l of cells containing 71.7% of a 3-hydroxybutyrate (HB)/3-hydroxyvalerate (HV) copolymer with a hydroxyvalerate content of 5 % (the remainder of the polymer being hydroxybutyrate).

The sample of the cells was first heat treated at 150° C. for 80 seconds at pH6.5. These heat shocked cells were then treated with a proteolytic enzyme. (EC 3.4.21.14) at pH8, 70° C. for 2 hours. At the end of this time the pH of the suspension was adjusted to pH7, the temperature raised to 80° C. and diethylene triamine penta methylene phosphonic acid added to give a final concentration of 6 mM. 35% w/v hydrogen peroxide solution was added to give a final aqueous phase concentration of $H_2O_2$ of 5.0% w/v. The temperature and pH conditions were maintained for 10 hours. The resulting polymer solids were recovered by centrifugation, washing and drying.

Analysis of the polymer product for impurities indicated that the concentration of residual nitrogen was 790 ppm corresponding to a protein concentration of approximately 5000 ppm.

The polymer product was thus considered to be 99.5% pure poly-3-hydroxybutyrate/3-hydroxyvalerate.

EXAMPLE 3

A strain of *Alcaligenes eutrophus* was grown in batch culture in an aqueous medium on a mixture of glucose and propionic acid under phosphorus limitation to give a culture containing 164.7 g/l of cells containing 72.1% of a 3-hydroxybutyrate (HB)/3-hydroxyvalerate (HV) copolymer with a hydroxyvalerate content of 8% (the remainder of the polymer being hydroxybutyrate).

The sample of the cells was first heat treated at 150° C. for 80 seconds at pH6.5. The pH of the heat shocked cell suspension was adjusted to 7 and the temperature adjusted to 80° C. Diethylene triamine penta methylene phosphonic acid added to give a final concentration of 2.5 mM. 35% w/v hydrogen peroxide solution was added to give a final aqueous phase concentration of $H_2O_2$ of 5.0% w/v. The temperature and pH conditions were maintained for 10 hours. The resulting polymer solids were recovered by centrifugation, washing and drying.

Analysis of the polymer product for impurities indicated that the concentration of residual nitrogen was 880 ppm corresponding to a protein concentration of approximately 5000 ppm.

The polymer product was thus considered to be 99.5% pure poly-3-hydroxybutyrate/3-hydroxyvalerate.

EXAMPLE 4

A strain of *Alcaligenes eutrophus* was grown in batch culture in an aqueous medium on a mixture of glucose and propionic acid under phosphorus limitation to give a culture containing 153 g/l of cells containing 68.8% of a hydroxybutyrate (HB)/3-hydroxyvalerate (HV) copolymer with a hydroxyvalerate content of 5% (the remainder of the polymer being hydroxybutyrate).

The cell suspension was adjusted to 7 and the temperature adjusted to 80° C. Diethylene triamine penta methylene phosphonic acid added to give a final concentration of 6 mM. 35% w/v hydrogen peroxide solution was added to give a final aqueous phase concentration of $H_2O_2$ of 5.0% w/v. The temperature and pH conditions were maintained for 10 hours. The resulting polymer solids were recovered by centrifugation, washing and drying.

Analysis of the polymer product for impurities indicated that the concentration of residual nitrogen was 890 ppm corresponding to a protein concentration of approximately 5000 ppm.

The polymer product was thus considered to be 99.5% pure poly-3-hydroxybutyrate/3-hydroxyvalerate.

EXAMPLE 5

A strain of *Alcaligenes eutrophus* was grown in batch culture in an aqueous medium on a mixture of glucose and propionic acid under phosphorus limitation to give a culture containing 160 g/l of cells containing 75% of a 3-hydroxybutyrate (HB)/3-hydroxyvalerate (HV) copolymer with a hydroxyvalerate content of 9% (the remainder of the polymer being hydroxybutyrate).

A sample of the cells was first heat treated at 150° C. for 80 seconds at pH6.5. These heat shocked cells were then treated with a proteolytic enzyme (EC 3.4.21.14) at pH8, 70° C. for 2 hours. At the end of this term the temperature of the solution was reduced to 20° C., the pH of the suspension was adjusted to pH7, diethylene triamine penta methylene phosphonic acid added to give a final concentration of 3 mM. 130 volume hydrogen peroxide solution was added to give a final aqueous phase concentration of 18 volume $H_2O_2$. The suspension was placed in a sealed pressure resistant glass tube, equipped with means for pressure and temperature measurement.

The tube containing the suspension was placed in an oven which had been adapted to contain the sample in the event of rapid depressurisation. The solution in the test tube reached 150° C. in 5 minutes and the temperature was maintained for in the first experiment for 10 minutes and in a second identical experiment, for 30 minutes. The solutions were then cooled to 20° C. in 15 minutes and the resulting polymer solids recovered by centrifugation, washing and drying.

Analysis of the polymer product for impurities indicating the purity of the polymer produced from reaction at 150° C. is given below.

| Residence Time at 150° C. (min) | Residual Nitrogen (ppm) | Residual Protein (ppm) | Polymer purity % |
|---|---|---|---|
| 10 | 1800 | 11,250 | 98.9 |
| 30 | 1540 | 9,625 | 99 |

If it is desired to carry out the process as a single stage, the $H_2O_2$ is added to the culture without intermediate treatment. The culture may then be heated as described and the polymer product recovered by centrifuging washing and drying.

We claim:

1. A process of recovering a plastic from a plastic producing microorganism in which non plastic material is removed from the plastic by a process which comprises a stage of chemically reacting non plastic material of the microorganisms with an oxidising agent in the presence of a chelating agent.

2. A process of producing a plastic which comprises growing a plastic producing microorganism under conditions conducive to plastic accumulation characterised in that non plastic material is removed from the product by a process which comprises chemically reacting non plastic material of the microorganisms in a stage of chemical solubilisation of non plastic material with an oxidising agent in the presence of a chelating agent.

3. A process in which the microorganism is physically conditioned before carrying out a process according to claim 1.

4. A process according to claim 3 in which the physical Conditioning comprises disrupting the cell wall and/or degrading nucleic acids at a temperature of 100° to 200° C.

5. A process according to claim 1 in which at least sufficient chelating agent is present to chelate any polyvalent metal ions which are present.

6. A process as claimed in claim 1 in which 10 to 30 oxygen equivalents of oxidising agent are supplied per kilogram of non plastic cellular material.

7. A process as claimed in claim 1 in which the oxidising agent is hydrogen peroxide.

8. A process as claimed in claim 1 in which the chemical reaction is carried out at a temperature of from 60° to 180° C.

9. A process as claimed in claim 1 in which the treatment with an oxidising agent is a first chemical treatment stage.

10. A process as claimed in claim 9 in which the treatment with an oxidising agent is the only chemical treatment stage.

11. A process as claimed in claim 1 in which the plastic is a polyhydroxyalkanoate.

12. A process as claimed in claim 11 in which the plastic is a polymer or copolymer of hydroxybutyric acid.

* * * * *